United States Patent
Andersson

(10) Patent No.: US 8,703,924 B2
(45) Date of Patent: Apr. 22, 2014

(54) CHITOSAN COMPOSITION

(75) Inventor: Mats Andersson, Uttran (SE)

(73) Assignee: Viscogel, AB, Solna (SE)

( * ) Notice: Subject to any disclaimer, the term of this patent is extended or adjusted under 35 U.S.C. 154(b) by 323 days.

(21) Appl. No.: 12/740,942

(22) PCT Filed: Oct. 30, 2008

(86) PCT No.: PCT/EP2008/064737
§ 371 (c)(1),
(2), (4) Date: Aug. 20, 2010

(87) PCT Pub. No.: WO2009/056602
PCT Pub. Date: May 7, 2009

(65) Prior Publication Data
US 2010/0316715 A1 Dec. 16, 2010

Related U.S. Application Data

(60) Provisional application No. 60/983,623, filed on Oct. 30, 2007.

(51) Int. Cl.
*C08B 37/08* (2006.01)
*A61K 31/722* (2006.01)
*A61K 47/36* (2006.01)
*A61K 47/38* (2006.01)
*A61K 8/73* (2006.01)
*A61K 9/14* (2006.01)
*A61K 9/52* (2006.01)
*A61P 37/04* (2006.01)
*A61P 13/00* (2006.01)
*A61P 43/00* (2006.01)

(52) U.S. Cl.
USPC .......... 536/20; 424/278.1; 424/488; 435/325; 435/404; 514/55; 514/777; 507/110; 106/162.2

(58) Field of Classification Search
None
See application file for complete search history.

(56) References Cited

U.S. PATENT DOCUMENTS

| 5,863,554 A | 1/1999 | Illum |
| 5,977,330 A | 11/1999 | Lohmann et al. |
| 6,806,260 B1 * | 10/2004 | Hirofumi et al. .............. 514/55 |
| 2003/0129730 A1 | 7/2003 | Chenite et al. |

FOREIGN PATENT DOCUMENTS

| WO | WO 2005/061611 | * | 7/2005 |
| WO | WO 2005/061611 A1 | | 7/2005 |
| WO | WO 2007/073749 A1 | | 7/2007 |

OTHER PUBLICATIONS

Onishi, H. et al "Biodegradation and distribution of water-soluble chitosan in mice" Biomaterials (1999) vol. 20, pp. 175-182.*
Berger, J. et al "Structure and interactions of covalently and ionically crosslinked chitosan . . . " Eur. J. Pharm. Biopharm. (2004) vol. 57, pp. 19-34.*
Sinha, V. et al "Chitosan microspheres as potential carriers for drugs" Int. J. Pharm. (2004) vol. 274, pp. 1-33.*
Kurita, K. et al "Solubilization of a rigid polysaccharide . . . " Carbohyd. Polym. (1991) vol. 16, pp. 83-92.*
De Angelis, A. et al "Synthesis of 13C CP-MAS NMR characterization . . . " Macromolecules (1998) vol. 31, pp. 1595-1601.*

* cited by examiner

*Primary Examiner* — Leigh Maier
(74) *Attorney, Agent, or Firm* — McDermott Will & Emery LLP

(57) ABSTRACT

This invention relates to a cross-linkable chitosan composition comprising chitosan having a degree of deacetylation between 30 and 75%, wherein the chitosan is randomly deacetylated, and a cross-linking agent, wherein the molar ratio of the cross-linking agent to chitosan is 0.2:1 or less based on the number of functional groups in the cross-linking agent and the number of accessible amino groups in the chitosan. The invention also provides a chitosan hydrogel formed therefrom and uses thereof.

10 Claims, 1 Drawing Sheet

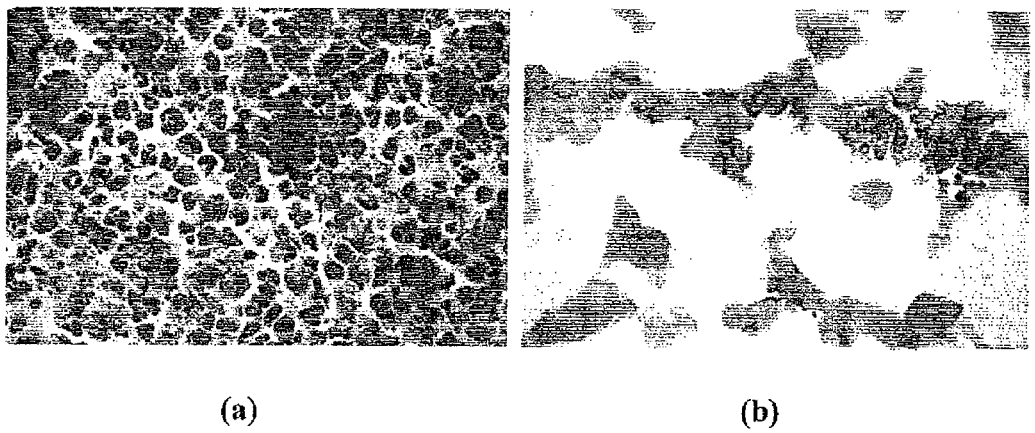
(a) (b)

CHITOSAN COMPOSITION

RELATED APPLICATIONS

This application is the U.S. National Phase under 35 U.S.C. §371 of International Application No. PCT/EP2008/064737, filed on Oct. 30, 2008, which in turn claims the benefit of U.S. Provisional Application No. 60/983,623, filed on Oct. 30, 2007, the disclosures of which applications are incorporated by reference herein.

This invention relates to a chitosan composition, and particularly to chitosan gels made from chitosan having a low degree of deacetylation and which is covalently crosslinked at a pH in the range of 6-10.

BACKGROUND TO THE INVENTION

The present invention relates to biocompatible polysaccharide gel compositions, and in particular chitosan compositions in vaccines, for drug delivery, tissue augmentation, cell culture, encapsulation of viable cells, cosmetic use, orthopaedic use, use as biomaterials, wound healing devices, thickener and additive in the food industry, use as glues, lubricants, drilling and servicing fluids. The gels are prepared by covalently cross-linked chitosan gels having a low degree of deacetylation. By choosing chitosans of specific degrees of deacetylation and using efficient cross-linking conditions gels with interesting and unexpected biological and physical properties could be obtained. This is in contrast to other cross-linked chitosan hydrogels, made from standard chitosan and using typical cross-linking protocols. The gels according to the invention can be made to have very low toxicity and they can be made to degrade rapidly. Another striking feature of said gels is that they do not precipitate when subjected to neutral and alkaline conditions. They also possess a rigidity which allows for further mechanical processing into e.g. injectable so called "crushed gels", useful in a vast number of applications.

A hydrogel could be defined as a colloidal gel in which water is the dispersion medium. Hydrogels are widely used in many fields and have become billion dollar industries in several areas. Typically hydrogels are made from water soluble polymers, which have been either isolated from natural sources or obtained by synthesis or by chemical modifications of natural polymers. These polymers are selected for their physical and biological properties and are used alone or in combinations depending on the desired product properties. Some polymers have physical properties that make them suitable for medical use whereas others are used in the food industry, mechanical processing and manufacturing industry, as lubricants, drilling and servicing fluids, in cosmetics, biomaterial applications, in biotechnology as cell scaffolds and more. The different applications require different qualities of the polymers and many technical applications are based on crude bulk qualities available at low cost, whereas highly purified qualities, often at high cost, are required for medical applications. Sometimes the physical properties of the polymeric solution, such as viscosity, are the main parameter of interest, whereas in other applications the biological and toxicological properties become more prominent for its function in the intended application.

Some polymers are used for filling purposes in tissue augmentation compositions in which gels are used either alone or together with solid beads. In other uses, e.g. wound healing, drug delivery, vaccine vehicles other polymers with other properties are desired to meet the medical demand. In general, properties like viscosity, anti-microbial activity, adhesive or water absorbing/retaining capacity are all properties that have to be considered. Water retention capacity and swelling are typically of great importance in food applications in which the polymer is used either as a thickener or as a solubility enhancer and stabiliser of other agents. There is a wide variety of polymers found in medical products, both synthetic and polymers of natural origin. In many applications it is important that the polymers degrade and are eliminated without causing unwanted side-effects. Even though biodegradability is not always necessary, a good biocompatibility is crucial in order to avoid side-reactions like inflammation, immunological reactions, or rejection of the material. Therefore it is not surprising that naturally occurring, non-toxic polysaccharides are used in medical products, as they have excellent physical properties in combination with interesting biological and medical properties and are usually available at high purity and low cost. Commonly used polysaccharides are e.g. cellulose, alginates, chitosan, hyaluronic acid, starch or derivatives thereof.

In medicine, gels and ointments are used e.g. for delivery of drugs, cosmetic purposes, or to give anti-bacterial barriers to avoid infection. Hydrogels have often relevant solubility and biological properties and are consequently found in a vast set of products. Gel forming polysaccharides like hyaluronic acid, derivatives of cellulose, and alike have become profitable industrial areas. Hyaluronic acid is an example of a polymer which could be used as such since it spontaneously forms hydrogels when used in low concentration water solutions at physiological pH. Other polymers like cellulose cannot be used, as such, and have to be chemically modified to get the desired properties. When preparing hydrogels from polysaccharides, a typical protocol involves dissolution of the polymer in an aqueous solution in low concentrations, often between 0.5 and 3% (w/w). When higher viscosities are desired this can be achieved by either adding more polymer to the solution, if solubility permits, or by cross-linking the polymers. Cross-linking gives polymers of higher molecular weight and consequently of higher viscosity. Cross-linking can be performed in different ways, using covalent, ionic or hydrophobic strategies and a huge number of approaches are available. In general when the product of such a cross-linking reaction is intended for medical use it is desirable to keep the cross-linking level as low as possible, since there is a risk for introducing immunological reactions toward the linker and it may also compromise the biodegradability.

Immunology and allergy. The immune system can be divided into innate and adaptive immunity. The innate or non-specific immunity is an inherent resistance manifested by a species that has not been immunised by infection or vaccination. Adaptive or acquired immunity is a type of immunity in which there is an altered reactivity against the antigen that stimulated it and which generates antigen-specific immunological memory. The immunity may be active i.e. a result of an acquired infection or a vaccination or it can be passive i.e. acquired from a transfer of antibodies. Passive vaccination with antibodies has several drawbacks: Injection of foreign substances may give rise to an immune response against the injected antibodies. Monoclonal antibodies must be injected in a large amount which makes this therapy very expensive. The treatment has to be sustained to maintain its function. Active vaccination to induce antibody formation and immunological memory is most often preferred. Most natural immunogens are proteins with a molecular weight above 5 kDa. Even immunogenic molecules may not generate the level of immunity desired. To increase the intensity of the immune response immunogens are combined with adjuvants. Adjuvants are agents that enhance the immune response without generating unwanted antibodies against the adjuvant. If the immunogen is still unable to generate an acceptable immune response, it may be conjugated to a carrier that is more immunogenic. Small molecules with molecular weight ranging from 0.1 to 2 kDa are often too small to be recognised by the immune system and thereby difficult to use as such in immunisations. One way of circumventing this is to bind them covalently to larger carrier molecules. Vaccination can be oral, nasal, subcutaneous, submucosal, sublingual, or intramuscular.

The recognition and destruction of foreign cells by T- and NK cells is termed cell-mediated immunity (TH1 immune response). Humoral immunity is associated with B-cells (TH2 immune response). Aluminium hydroxide has been reported to selectively activate TH2 cells whereas Freund's complete adjuvant activates TH1 cells. Chitosan has been shown to enhance both humoral and cell-mediated immune response (Vaccine 3, 379-384, 1985).

The innate immune system recognises a wide spectrum of pathogens without a need for prior exposure. The main cells responsible for innate immunity, monocytes/macrophages and neutrophils, phagocytose microbial pathogens and trigger the innate, inflammatory, and adaptive immune responses. Toll-like receptors (TLRs) are a family of type I transmembrane proteins involved in the recognition of a wide range of microbes. They play a key role in the innate immune system. TLRs are a type of pattern recognition receptors (PRRs) and recognise molecules that are broadly shared by pathogens but distinguishable from host molecules, collectively referred to as pathogen-associated molecular patterns (PAMPs). Macrophage receptors are also considered to be pattern-recognition receptors. The macrophage mannose receptor recognises hexoses with equatorially placed hydroxyl groups at carbons C3 and C4, positions enabling the recognition of mannose, fructose, N-acetylglucosamine and glucose (Curr. Opin. Immunol. 10, 50-55, 1998).

Allergy is a very common disorder affecting approximately one fourth to one third of the population in industrial countries, e.g. more than 50 million Americans suffer from allergic diseases. The treatment strategy by far most commonly used today is to target the effector mechanisms of allergy, e.g. by oral ingestion of antihistamines or by topical corticosteroids. Antihistamine and corticosteroid treatment can be effective in relieving allergy symptoms, but their use leads to exposing the entire body to the pharmaceutical product, and they may produce unpleasant or even harmful side effects. Allergen-specific immunotherapy is the only treatment in use that targets the underlying causes of allergy and that gives long-lasting symptom relief. It may thus be considered as the only curative treatment for allergic disease. This treatment may be given as subcutaneous injections or sublingually. Carried out by injecting allergen extracts subcutaneously it has a well-documented effect, while the efficacy of sublingual allergen-specific immunotherapy is less documented.

Allergic diseases such as asthma and rhinitis are caused by an inappropriate immune response to otherwise harmless environmental antigens, i.e. allergens. The most common form is Immunoglobulin (Ig) E-mediated allergy, characterised by the presence of allergen-specific IgE. There are currently two general strategies to treat IgE-mediated allergies, pharmacological therapy and allergen-specific immunotherapy. Pharmacological treatment includes treatment with topical corticosteroids, especially in the case of allergic asthma and eczema. However, 10-20% of the patients with allergic asthma do not respond to steroid treatment. Other common anti-allergy drugs target effector mechanisms of IgE-mediated allergy, e.g. antihistamines, antileukotrienes and chromones. The only curative therapy of IgE-mediated allergy, i.e. the only treatment that gives long-lasting relief of symptoms, is allergen specific immunotherapy (ASIT). In contrast to pharmaceutical treatment, ASIT has also been shown to reduce airway inflammation and protect against development into chronic asthma (J Allergy Clin Immunol. 1998 102(4 Pt 1), 558-62). The treatment is based on the repeated administration of allergen in order to induce allergen-specific unresponsiveness. At present, allergen extracts prepared from natural sources and adsorbed to aluminium hydroxide (alum) are commonly used in ASIT. Alum delays the release of allergen and acts as an adjuvant. However, there are some drawbacks linked to the use of allergen extracts and alum. Many injections with low allergen doses are required during a time period of 3-5 years. To solve problems like induction of new sensitisations and adverse side-effects to extracts, recombinant allergens have been proposed for use in ASIT (Adv Immunol. 2004; 82:105-53, Nat Rev Immunol. 2006 October; 6(10):761-71). Recombinant allergens can be modified in different ways with the aim to achieve safer and more efficient protocols for ASIT. Examples of such novel strategies are to create so called hypoallergens, i.e. allergens with reduced IgE binding capacity but retained T-cell activity, vaccination with allergen-derived peptides or coupling of allergens to immunomodulating agents such as immunostimulatory oligonucleotides containing CpG motifs (Nat Rev Immunol. 2006 October; 6(10):761-71, Curr Opin Immunol. 2002 December; 14(6):718-27). Alum is known to cause granuloma at the injection site and to mainly stimulate Th2 responses. Consequently alternative adjuvants are needed for ASIT.

Adjuvants are substances that enhance the ability of an antigen to elicit an immune response. Even though extensive efforts to develop new adjuvants for human vaccines are made, the only widely used adjuvant is still aluminium hydroxide. It has been shown that aluminium adjuvants can cause neuron death. The development of novel adjuvants is desirable in order to maximise the efficiency of new vaccines. An ideal adjuvant should give long lasting expression of functionally active antibodies, elicit cell-mediated immunity and enhance the production of memory T and B lymphocytes with highly specific immuno-reactivity against an antigen. It should provide both an immediate defense and a protection against future challenges with an antigen. It should also be biodegradable, non-toxic and not give rise to an immune response directed towards the adjuvant itself.

Vaccinations should give a long-lasting effect, fast antibody production and high antibody titres.

The use of chitin and chitosan as adjuvant has been mentioned in U.S. Pat. No. 4,372,883 and U.S. Pat. No. 4,814,169. The use of chitosan in vaccines in the form of solutions, dispersions, powders or microspheres has been described in U.S. Pat. No. 5,554,388, U.S. Pat. No. 5,744,166, and WO 98/42374. Cross-linking of chitosan switches the immune response from a TH2 towards a mixed TH1/TH2 response. The use of chitosan solutions mixed with antigens for immunisations show that chitosan is equipotent to Freund's incomplete adjuvant and superior to aluminium hydroxide (Vaccine 11, 2085-2094, 2007).

Drug delivery. Drug delivery is a very intense research area and a lot of money is today spent on finding new and improved formulations that deliver pharmaceutical active ingredients like low molecular drugs, genes, and vaccines more specifically and at the same time minimises unwanted side effects. Old drugs become new in new and improved formulations.

The properties of chitosan, physical and biological, have made it very suitable for delivery of pharmaceutically active components and as a delivery vehicle for e.g. vaccines, gene fragments and micro-RNA. Useful and important features of chitosan is that it to bind to all living tissue, has mucoadhesive properties, is degradable and opens tight junctions between cells. By taking advantage of these properties, drug delivery over the mucous membrane can be dramatically improved. Drug formulations based on chitosan technology are today under development for different purposes e.g. as vaccine carriers, drug releasing hydrogels, membranes, gauze and more. Chitosan has shown to be useful in e.g. colon delivery (H. Tozaki, et. al, J. Pharm., Sci., 86, 1016-1021, 1997) and intranasal delivery of insulin (U.S. Pat. No. 5,744, 166). Chitosan has also been used as a carrier in gene delivery (MacLaughlin, et. al, J. Controlled Release, 56, 259-272, 1998).

Some formulations are designed to give a sustained release over time whereas release from others are more instant. When a hydrogels of chitosan are used it has been found that cross-linking is preferred since gels without cross-linkers have a tendency to dissolve. Another advantage of using cross-linking is that the release rate from the gel can be altered by using different degrees of cross linking. Chitosan can be used for development of new formulations for e.g. oral, dermal, subcutaneous, buccal, sublingual, nasal, rectal, vaginal and intra muscular administration.

Many drugs that are administered in an unmodified faun by conventional systemic routes fail to reach the target organs in an effective concentration, or are not effective over a length of time due to a facile metabolism. By use of a Drug Delivery Systems (DDS), it is possible to overcome these problems.

Cancer drugs are often characterised by a short plasma half-life and/or by remarkable side effects. An approach to reduce these problems may be via focal administration, i.e. local drug delivery at the site of the cancer via implantation/injection of a DDS containing the chemotherapeutic agent. In comparison with systemic administration, the extent of side effects will decrease and the total effect of the drug will increase.

When developing a DDS for focal therapy of cancer, several technical factors have to be taken into consideration, namely biocompatibility, biodegradable (importance depends on disease, site of application and number of administrations), sterility/sterilisation, compatibility with drugs and pharmaceutical excipients, ease of administration (via syringe is preferred), flexibility regarding the dose, drug load, dose positioning, ability to control release rate of drug and patient acceptability, as well as consideration of regulatory hurdles, CoG (cost of goods), and IPRs.

By injection of the DDS with drug results in the localisation of a greater amount of the loaded drug at the tumour site, thus improving cancer therapy and reducing the harmful non-specific side effects of chemotherapeutics.

Tissue augmentation. Tissue augmentation can be used for both medical and cosmetic purposes. A medical application is, for example, augmentation of tissues in order to obtain improved function of the tissue. Examples of tissues that can be strengthened by injection of bulking agents are the vocal cords, the oesophagus, urethra or rectum. In the area of cosmetic surgery, soft tissue augmentation may be used to correct defects as scars and wrinkles and to enlarge for example lips or breasts. A variety of different materials, both non-biodegradable and biodegradable, has been used to repair or augment soft tissue. Examples of materials used for permanent soft tissue augmentation are silicone, Gore-Tex, and ePTFE. Examples of biodegradable materials are collagen, autologous fat, cross-linked hyaluronic acid, and synthetic polymers.

Silicone is one of the most frequently used materials for permanent soft tissue augmentation. Adverse reactions to liquid injectable silicone include granulomatous reactions, inflammatory reactions, and drifting. These reactions can occur years after initial treatment. Furthermore, since injectable silicone is a permanent filler, the above complications can become a serious problem since the substance will not be metabolised and the reaction can persist despite treatment.

Collagen is one of the most frequently used injectable materials, both for cosmetic applications and as a bulking agent for e.g. urinary incontinence. Collagen, however, has several drawbacks. It degrades rapidly and approximately 3% of the population show delayed hypersensitivity reactions, which makes it necessary to perform allergy tests over a period of time prior to injection. Furthermore, collagen of bovine origin may transmit viral diseases.

Autologous fat injections are well known. These materials also have disadvantages. Fat injected into facial lines and wrinkles have caused loss of vision and embolism in some patients. Furthermore autologous fat is readily absorbed by the body.

Cross-linked hyaluronic acid products are used both for cosmetic treatments and as bulking agents for the treatment of e.g. urinary incontinence (UI) and vesicoureteral reflux (VUR).

A common approach in the design of bulking agents is to use spheres of a non-biodegradable material dispersed in a biologically degradable carrier. Examples include carbon-coated beads in a beta-glucan gel, hydroxyapatite spheres in carboxymethyl cellulose, polytetrafluoroethylene particles and poly(lactic-co-glycolic acid) (PLGA) microspheres. One risk with particle injections is the potential particle migration to distant organs such as brain and lungs.

The existing materials are not optimal and there is a continuing search for new materials for tissue augmentation applications, materials that are injectable through thin needles, biocompatible, non-toxic and with suitable residence time in the tissue.

Chitosan gels for soft tissue augmentation have been described (WO 97/04012, EP 1 333 869).

Chitosan gels have also been used in the cultivation of cells and for incorporation of viable cells to be used in e.g. cartilage tissue engineering as described in for example Biomaterials. 2000; 21(21):2165-61, J Biomed Mater Res A. 2007; 83(2): 521-9, and Biochimie. 2006; 88(5): 551-64.

In cosmetics chitosan has been used in for example skin creams (US 20060210513, US 20040043963) and to decrease skin irritation caused by shaving (U.S. Pat. No. 6,719,961).

Chitosan may also be used as a lubricant (Nature. 2003, 425:163-165). The use of chitosan as a thickener has been described in e.g. Environ Sci Technol. (2002) 36(16):3446-54 and Nanotechnology (2006) 17 3718-3723. It has also been used as a glue (Biomacromolecules. 1(2):252-8 (2000) and Fertil Steril, 84, 75-81 (2005)) and as a dietary supplement (U.S. Pat. No. 5,098,733, U.S. Pat. No. 5,976,550, U.S. Pat. No. 6,238,720 and U.S. Pat. No. 6,428,806).

In addition to the medical applications, viscoelastic chitosan hydrogels may be used as pseudoplastic, shear thinning chitosan-containing fluids, and a method of enhancing the thermal stability of such fluids is described in for example U.S. Pat. No. 6,258,755, Chitin is next to cellulose the most abundant polysaccharide on earth. It is found in hard structures and strong materials in which it has a function of a reinforcement bar. Together with calcium salts, some proteins and lipids it builds up the exoskeletons of marine organisms like crustaceans and arthropods. It is also found in the cell walls of some bacteria and sponges and build up the hard shells and wings of insects. Commercially, chitin is isolated from crustacean shells, which is a waste product from the fish industry. Chitosan is a linear polysaccharide composed of 1,4-beta-linked D-glucosamine and N-acetyl-D-glucosamine residues. Chitin in itself is not water soluble, which strongly limits its use. However, treatment of chitin with strong alkali gives the partly deacetylated and water-soluble derivative chitosan which can be processed in a number of different physical forms, e.g. films, sponges, beads, hydrogels, membranes. Chitosans in their base form, and in particular those of high molecular weight, and/or high degrees of N-deacetylation, are practically insoluble in water, however its salt with monobasic acids tend to be water-soluble. The average pKa of the glucosamine residues is about 6.8 and the polymer forms water-soluble salts with e.g. HCl, acetic acid, and glycolic acid. The solubility of chitosan depends on several factors, both intrinsic as e.g. chain length, degree of deacetylation, acetyl group distribution within the chains, but also external conditions such as ionic strength, pH, temperature, and solvent. From literature it is known that a degree of acetylation of about 50% is optimal for solubility. When making gels and water solutions in an acidic environment there is a practical limit set by the solubility of the specific chitosan, which is dependent on its molecular weight and its degree of N-deacetylation. However, the amount of chitosan in an aqueous medium is typically in a range from 1-10%, or 1-5%, by weight based on the weight of the liquid medium, with the amount tending towards the higher end of the range if low molecular weight chitosans are used (Carbohydr. Polym. 25, 65-70, 1994).

The inherent properties of chitosan, being biodegradable, non-toxic and anti-microbial in combination with its cationic and hydrophilic nature makes it attractive in pharmaceutical formulations. However, its poor solubility at physiological conditions has limited its practical use. Scientists have circumvented this shortcoming of solubility by making chemically modified chitosan derivatives with superior solubility properties at physiological pH e.g. sulphated chitosan, N-carboxymethyl chitosan, O-carboxymethyl chitosan and N,O-carboxymethyl chitosan (Int J Biol Macromol. (4), 177-80, 1994, Carbohydr Res. 302(1-2):7-12, 1997).

A consequence of introducing chemical substituents on chitosan will be changed biological properties e.g. altered degradation rate and the risk for introducing groups that will have a negative impact on biocompatibility and toxicity. This problem has been addressed in U.S. Pat. No. 6,344,488 in which glycerophosphate is used as a solubility enhancer and thus allows preparation of chitosan hydrogels at physiological pH, without the modification of the chitosan structure.

Chitosan solutions can be cross-linked under acidic conditions, typically at suitable for Shiff base formation (pH 4-5), to form hydrogels. A huge number of different cross-linkers with different structures and reactivities have been used. Several cross-linking agents have been used in order to form gels from liquid chitosan, for example glycosaminoglycans such as hyaluronic acid and chondroitin sulfate (Ann. Pharm. Fr. 58 47-53, 2000), glutaraldehyde (Ind. Eng. Chem. Res. 36: 3631-3638, 1997), glyoxal (U.S. Pat. No. 5,489,401), diethyl squarate (Macromolecules 31:1695-1601, 1998), diepoxides such as diglycidyl ether (U.S. Pat. No. 5,770,712), tripolyphosphate (J Appl Polym Sci 74: 1093-1107, 1999), genipin (J Polym Sci A: Polym Chem 38: 2804-2814, 2000, Biomaterials. 23:181-191, 2002), formaldehyde (J. Polym. Sci. Part A: Polym. Chem. 38, 474, 2000, Bull. Mater. Sci., 29, 233-238, 2006). When a hydrogel is the desired product it is mandatory that chitosan and its derivative remain in solution and that precipitation thereof is avoided. Attempts to adjust the pH of cross-linked chitosan hydrogels, to physiologically acceptable levels, result in precipitation and insoluble materials of limited use. It is desirable to keep the degree of cross-linking as low as possible, both for toxicology reasons and also because a high degree of cross-linking may alter the behaviour of chitosan completely (Eur J Pharm Biopharm. 2004, 57(1):19-34. Review).

A specific group of hydrogels are the viscoelastic gels, gels that are viscous and at the same time show elastic properties. A viscoelastic gel will deform and flow under the influence of an applied shear stress, but when the stress is removed the liquid will slowly recover from some of the deformation. This is used in e.g. ophthalmology, tissue augmentation, and cosmetic surgery. The viscoelasticity of the gels allow for mechanical processing which includes the preparation of crushed gels. Viscoelastic gels of hyaluronic acid are e.g. used in eye surgery, wrinkle filling or in the treatment of urinary incontinence.

Chitosan, a natural polyelectrolyte. The three dimensional orientation of a polyelectrolyte in an aqueous environment will be dependent on e.g. its nature/chemical composition, size, concentration and charge density, i.e. the number of charges and the distance between its charged groups. The spatial interactions of any polyelectrolyte in a solution will be controlled by enthalpy and the molecule will strive to adapt a low energy state in which it is most stable. This energy minimisation process involves different types of interactions, either intra-molecular (within the same molecule) or intermolecular (between molecules). Examples of intra-molecular interactions are hydrogen bonds, hydrophobic interactions and interactions between charged groups on the polymer. Typical inter-molecular interactions are solvent interactions and interactions with other molecules. Irrespectively of the type of interaction involved, the driving force for these interactions is to find energetically favourable conformations of the polyelectrolyte.

When a polyelectrolyte contains charged groups having the same type of charge, e.g. positive, the groups will repel each other. In order to reduce its internal energy the polyelectrolyte molecule will strive to separate its internal charges as much as possible, which will lead to a stretched polymer chain. These stretched polymers will not only be more "space demanding", they will also have a relatively high state of energy harboured in the constrained linkages between atoms.

On the other hand, if the polyelectrolyte contains charges of opposite signs, they will attract each other and form internal salt bridges which will result in a different three dimensional orientation of the polymer, i.e., different parts of the polymer are brought closer to each other. In a polymer without any charges, there are no ionic interactions and consequently its three dimensional orientation will depend on its ability to foam stabilising hydrogen bonds and hydrophobic interactions within the molecule and with the surrounding molecules and the media. In contrast to the polyelectrolytes, the uncharged polymers that do not contain any high energetic repulsive forces, from some kind of "random coil" structure in which their internal energy has been minimised and their relative energy content is lower than that of the polyelectrolytes.

Physically, ionic interactions (charges) are much stronger and involve more energy than other interactions like, hydrogen bonds, van der Waals forces and hydrophobic interactions. The relative impact of the former on the molecular orientation is thus large and will in many cases overshadow the impact of the other types of forces involved.

The chitosan polymer with its mix of N-acetyl-glucosamine and glucosamine residues could theoretically be a neutral polymer but in most practically and biologically relevant situations it will be protonated, since the pKa value for the glucosamines in chitosan is approximately 6.8. However, in contrast to polyelectrolytes bearing permanently charged groups, the charge density of a chitosan polymer can be varied and will be directly dependent on the pH of a water solution. Practically, most commercially available and unmodified chitosans are insoluble in water solutions when the pH is above approximately 6 and above this pH they will precipitate from an aqueous solution. The precipitation is energetically driven as the chitosan molecule requires a large number of charges on its molecular backbone to form an energetically favourable state of solvatisation. If this can not be accomplished; the molecules will precipitate from solution and faun more stable precipitates. In the precipitate, the chitosan chains have been brought together which allows for energy optimisations by molecular interactions between and within the chitosan molecules.

In order to increase the viscosity of a chitosan solution chemical cross-linking can be used. In such a reaction the chitosan chains are linked together to form larger network like aggregates. During such a reaction the viscosity successively increases and the solution becomes more gel-like in its structure. There is a large number of cross-linking procedures described for chitosan in solution and they have in common that the chitosan is dissolved in an acidic water phase and the cross-linking reaction takes place in at low pH, typically from 4-5. The low pH used implies that the chitosan chains are in their protonated form and they are consequently in a "stretched" form when cross-linked. The resulting cross-linked gel is then technically a macro structure of protonated and stretched chitosan chains. When such a macro network, is brought to neutral or alkaline conditions, it will gradually lose its charges, collapse and eventually precipitate. This is to some extent expected, since when standard chitosans, (degree of deacetylation between approximately 80-95%) are brought to a pH above 6 they precipitate. The cross-linking in itself has generated even larger electrolyte structures which will be even more demanding to stabilise in a water solution from an energy point of view. This is because positive charges have been brought closer together in the junction points between chains and thus will be even more difficult to stabilise with solvating water molecules. Consequently they are even more prone to precipitate than the individual chains when solution conditions are turned in a less energetically optimal way, e.g. pH is raised. Through the cross-links the macro gel structure has been locked in a stretched and energetically unfavourable state, which physically does not allow rearrangement to coils and other conformations that can contribute to more energetically favoured conformations resulting in higher stability of the system.

The precipitation of chitosan gels, formed in acidic conditions, is easily experimentally confirmed by subjecting a lump of such a cross-linked chitosan gel to a pH above seven or even higher values, i.e. pH 7-14. Immediately when such a lump is placed in a buffer of higher pH the surface of the lump becomes whitish by a thin layer of precipitate and as diffusion goes on, the lump becomes more and more whitish until it is fully precipitated.

However, and surprisingly we have found that this collapse of cross-linked chitosan gel macro structures can be circumvented by using low deacetylated chitosan of specific degrees of deacetylation and cross-linking the chitosan chains in an energetically less constrained conformation. Gels produced according to this procedure can be treated with 1 M sodium hydroxide without forming precipitates. A corresponding non-cross-linked gel will precipitate when treated with 1M NaOH.

By using the higher solubility of these specific chitosans, pH can be brought much higher during the cross-linking reactions. The advantages of doing this are numerous. Firstly the protonation of the chitosan chain becomes low and the chitosan polymer is almost neutral at pH above eight, allowing the formation of less constrained and more random coil like network in the solution. When the chitosan is subjected to cross-linking in this state the resulting gel structure will be built up by individual chitosan chains of higher flexibility and which will make them more easily reorganised to more energetically favoured macro structures when conditions are changed. Secondly, the possibility to use a higher pH is beneficial in terms of substantially increased reactivity of the amino groups on the glucosamine residues. This makes the couplings more efficient and enables the use of much lower concentrations of cross-linking reagents to reach a defined degree of cross-linking. Another benefit is that the side reactions are kept low. These cross-linked gels have several advantages compared to chitosan gels prepared at low pH and from standard grade chitosans (degree of deacetylation 80-95%). The fact that they do not precipitate at physiological conditions implies that they are more accessible to degrading enzymes, which leads to fast degradation of the gels, but also other properties as described in the present specification.

BRIEF DESCRIPTION OF THE INVENTION

Accordingly, the present invention provides a cross-linkable chitosan composition comprising chitosan having a degree of deacetylation between 30 and 75%, wherein the chitosan is randomly deacetylated, and a cross-linking agent, wherein the molar ratio of the cross-linking agent to chitosan is 0.2:1 or less based on the number of functional groups in the cross-linking agent and the number of accessible amino groups in the chitosan.

The present invention enables formation of a cross-linked, viscoelastic chitosan hydrogel at physiological pH without using other solubility enhancers, e.g. glycerophosphate.

One aim of the present invention is to provide a viscoelastic gel from chitosan which can be delivered at physiological pH without precipitating.

One object of the invention is to provide a viscoelastic gel that by chemical cross-linking has been given a physical strength that allows further processing into smaller, individually separated gel fragments, e.g. a crushed gel.

Another object of the invention is to provide a viscoelastic chitosan hydrogel that can be delivered via a fine syringe needle, typically such needles that are used for injections, e.g. for vaccination.

Another object of the invention is to provide a crushed viscoelastic chitosan hydrogel that exposes a large surface area and consequently becomes easily available for enzymes and invading cells, when used in vivo.

Another object of the invention is to provide a rapidly degrading viscoelastic chitosan hydrogel.

Another object of the invention is to provide a viscoelastic chitosan hydrogel of low toxicity and minimise or totally avoid unwanted immunological or toxicological reactions by using low concentrations of cross-linking agents, preferably agents of low toxicity or non-toxic agents.

Another object of the invention is to provide a viscoelastic chitosan hydrogel that allows incorporation of antigens and immunogens during its manufacturing, either covalently or non-covalently.

Another object of the invention is to provide a viscoelastic chitosan hydrogel having inherent adjuvant properties.

Another object of the invention is to provide a biodegradable, viscoelastic chitosan hydrogel for immunological use.

Another object of the invention is to provide a vehicle for delivery of antigens and immunogens intended for immunisations. The present invention provides an immunological agent comprising the chitosan hydrogel as described herein and an antigen, wherein the antigen is optionally covalently bonded to the chitosan.

Another object of the invention is to provide a viscoelastic chitosan hydrogel that allows for covalent incorporation of molecules resulting in an immunological response. Said molecules could be of either low or high molecular weight, e.g. small molecules like peptides, lipids, steroids and antibiotics or large molecules like proteins, gene fragments, microRNA, carbohydrate polymers and synthetic polymers.

Another object of the invention is to provide a viscoelastic chitosan hydrogel containing more than one immunogenic substance. The gel could be made to contain two or more antigenic molecules or mixtures of antigens of low and/or high molecular weight.

Another object of the invention is to provide a viscoelastic chitosan hydrogel that allows for the incorporation of other agents either covalently or non-covalently, e.g. preservatives, and other polymeric materials.

Another object of the invention is to provide a viscoelastic chitosan hydrogel, the release properties of which could be further altered by coating with anionic polymers. By using both cationic and anionic polymers in sequence multilayer coated viscoelastic gel structures could be constructed.

Another object of the invention is to provide a viscoelastic chitosan hydrogel for use in adjuvant immunotherapy in order to boost the immune response unspecific ally.

Another object of the invention is to provide a formulation that gives sustained release of the incorporated bioactive agents or antigens (e.g. allergens) by incorporating these in a viscoelastic chitosan hydrogel.

Another object of the invention is to provide a viscoelastic chitosan hydrogel for use in tissue augmentation, either alone or together with solid beads.

Another object of the invention is to provide a viscoelastic chitosan hydrogel for the treatment of e.g. urinary incontinence (UI) and vesicoureteral reflux (VUR).

Another object of the invention is to provide a viscoelastic chitosan hydrogel for use as a bulking agent.

Another object of the invention is to provide a viscoelastic chitosan hydrogel as cell culture scaffold.

Another object of the invention is to provide a viscoelastic chitosan hydrogel for use in providing living cells to a host organism.

Another object of the invention is to provide a viscoelastic chitosan hydrogel for oral, nasal, subcutaneous, submucosal, sublingual, corneal, rectal, vaginal or intramuscular drug delivery. The present invention provides a pharmaceutical composition comprising the chitosan hydrogel as described herein and a pharmaceutically active ingredient.

Another object of the invention is to provide a viscoelastic chitosan hydrogel that allows incorporation and release of drug, e.g. for focal cancer therapy as described hereinabove.

Another object of the invention is to provide a viscoelastic chitosan hydrogel that allows for incorporation of drugs during its manufacture, either covalently or non-covalently.

Another object of the invention is to provide a viscoelastic chitosan hydrogel for use as a wound healing device.

Another object of the invention is to provide a viscoelastic chitosan hydrogel for viscosurgery.

Another object of the invention is to provide a viscoelastic chitosan hydrogel for cosmetic use.

Another object of the invention is to provide a viscoelastic chitosan hydrogel for use as a lubricant.

Another object of the invention is to provide a viscoelastic chitosan hydrogel for use as glue.

Another object of the invention is to provide a viscoelastic chitosan hydrogel for use as a drilling or servicing fluid.

The present invention will now be described with reference to the accompanying drawing in which FIG. 1 shows histological sections from the injection sites of mice 24 hours after subcutaneous injection with the viscoelastic chitosan gel of the present invention and a comparative gel.

DETAILED DESCRIPTION OF THE INVENTION

The present invention relates in general to hydrogels made from chitosan intended e.g. for use in human or veterinary medicine. More specifically the present invention is aiming for chitosan hydrogels with viscoelastic properties for use according to the previous description. Thus according to the invention is provided a composition comprising chitosan or mixtures of chitosans of different degrees of deacetylation that does not precipitate under physiological conditions and at the same time exposes a large surface area thereby facilitating further biological processing. Compared to a chitosan solution according to prior art the surface area of the viscoelastic hydrogel according to the present invention is several magnitudes larger. This feature of the viscoelastic hydrogel of the present invention gives rise to faster cell infiltration and a more rapid immune response when it is subcutaneously injected in mice compared to chitosan solutions according to prior art (Vaccine 11, 2085-2094, 2007). This opens the possibility to use lower doses of the immunogen.

This is achieved by providing a cross-linkable chitosan composition comprising chitosan having a degree of deacetylation between 30 and 75%, wherein the chitosan is randomly deacetylated, and a cross-linking agent, wherein the molar ratio of the cross-linking agent to chitosan is 0.2:1 or less based on the number of functional groups in the cross-linking agent and the number of accessible amino groups in the chitosan. The chitosan hydrogel of the present invention is prepared by providing this cross-linkable chitosan composition in an aqueous solution, cross-linking the composition and isolating the resultant chitosan hydrogel. The present invention also provides a hydrogel obtainable by this process.

The solubility of chitosan depends on several factors, both intrinsic as e.g. chain length, degree of deacetylation, acetyl group distribution within the chains, but also external conditions such as ionic strength, pH, temperature, and solvent. Numerous attempts have been made to make physiological chitosan solutions and gels for medicinal use but most often with poor results. Most commercial chitosans have a degree of deacetylation exceeding 80% and when solutions and gels are made a low pH is required to dissolve the polymers, typically acidic solutions of acetic acid or hydrochloric acid are used. Attempts to raise the pH of such solutions result in precipitation of the chitosan polymer when the pH exceeds approximately 6. This problem can be circumvented by use of more water-soluble chitosan derivatives or by using additives like glycerophosphate. We have found that chitosan of low degree of deacetylation e.g. 50% can be used for preparation of hydrogels at physiological conditions and that chitosan concentrations up to a few percent can be made. The commercial availability of chitosans of low degrees of deacetylation is limited but the manufacture of such chitosans is described in the literature. One way of making chitosans of low degrees of deacetylation is to reacetylate chitosan under acidic conditions and then deacetylate. Another approach is to start deacetylation from chitin which has been taken into solution under strongly alkaline and cold conditions. Chitosans of low degrees of deacetylation, e.g. 50%, are not just more soluble than chitosans of higher degrees of deacetylations they are also faster and more easily cleaved by hydrolytic enzymes that require N-acetyl groups for recognition of cleavage sites. A less obvious but also important advantage of bringing chitosan gels and solutions to physiological pH levels is the concomitant increase in reactivity of the glucosamine residues in the polymeric chain. Under certain circumstances this could be utilised to suppress unwanted side reactions and to minimise the impact of potential cross-linkers since their concentrations could be kept much lower as an effect of the increased reactivity of the amino groups which gives a more efficient coupling. An illustrative example of this is when chitosan is cross-linked by use of a large excess of diethyl squarate under acidic conditions. In this reaction which is performed at a pH of about 4.75 almost 50 percent of the reagent added is hydrolysed in one of its two reactive sites, giving a squaric acid substituted chitosan chain which is not further cross-linked. When the same reaction is performed at pH above 7 reactivity is increased by several magnitudes and competing side reactions are suppressed, leading to clean and efficient reactions with a minimum of reagent to achieve the desired cross-linking network. This is most important when the chitosan gel structures are intended for immunological use. There are several reasons for this. Firstly there is always a risk for unwanted immunological reactions against the linker, secondly there is a risk for altered degradation kinetics, and thirdly cross-linkers as such are generally highly reactive and may cause toxic side reactions if not fully consumed, thus it is important to keep the level of these agents as low as possible. We prefer to use cross-linking reagents of low toxicity and to use cross-linkers that do not eliminate groups that have to be removed prior to biological use of the viscoelastic hydrogel. Dibutyl squarate is approved by the FDA for use as a topical immunomodulator and is not mutagenic in the Ames assay. Another commonly used group of cross-linker are reactive species based on epoxide chemistry. Diglycidyl ethers are frequently used for various cross-linking reactions in which they react with carboxylic acids, alkoxides, and amines. When diglycidyl ethers or a similar derivative has been used for cross-linking purposes of chitosan, fairly high ratios of the cross-linker to chitosan amino function have been used. This is illustrated in Journal of Biomedical Materials Research Part A, 2005, 75A, 3, 742-753 Eur. J. Pharm. Biopharm. 2004, 57: 19-34, U.S. Pat. No. 5,770,712, WO 02/40070. We have tried other cross-linking methods according to the literature. Glutaraldehyde cross-linking resulted for example in coloured hydrogels that precipitated when subjected to alkaline media. The viscoelastic hydrogel according to the invention can easily be coated with e.g. anionic polymers in order to alter the biological processing rate. When a viscoelastic hydrogel according to the invention is dialysed against alkaline media the surface of the gel remains clear whereas dialysis of a gel according to the prior art gives precipitation of the chitosan which is seen as an opaque gel surface. There is a dramatic difference in precipitation between a non-cross-linked and a cross-linked hydrogel. Surprisingly these gels were possible to treat with 1M NaOH without precipitating.

The structure of a viscoelastic gel is affected by the concentration of the chitosan solution and the amount of cross-linking reagent used. We prefer to have higher chitosan concentrations and lower concentrations of cross-linking agent to achieve a gel of the desired nature. A cross-linking molecule in this context has at least two reactive sites which are electrophiles designed to easily react with amines in neutral or slightly alkaline conditions. When the cross-linker has two reactive sites it is bifunctional and can thus react with two amino groups e.g. two glucosamine units in different chitosan chains. There are a number of commercially available cross-linking reagents of this nature and sometimes the distance between the reactive groups have been increased by a "spacer molecule". This spacer is often an aliphatic chain or a polyether construct like poly- or oligoethylene glycols. Preferably the cross-linking agent is bi-, tri- or tetrafunctional, although bi- or trifunctional is preferred and bifunctional is most preferred. We prefer to use bi-functional, cross-linkers that easily react under neutral to weakly alkaline conditions in high yielding reactions and in which the cross-linking molecule is consumed to high extent. We also prefer that the cross-linking molecule does not form by-products that have to be removed prior to use. Many cross-linkers are designed to eliminate a leaving group when reacting. In such cases we prefer cross-linkers that eliminate non-toxic components. Typical examples of such cross-linking functionalities are reactive esters, Michael acceptors and epoxides. Preferred cross-linking molecules are ester derivatives of squaric acid, diepoxides and derivatives of acrylamides. Most preferred is diethyl squarate (3,4-diethoxy-3-cyclobutene-1,2-dione) and its structurally closely related analogues. Other preferred cross-linkers are 1,4-butandiol diglycidylether, derivatives of acrylamide and their structurally closely related analogues.

It is also important to minimise the amount of cross-linking reagent and to get an efficient and clean coupling reaction, generating few if any side products. We prefer to use a low molar ratio of the cross-linking agent to the number of amino functions in the chitosan. We prefer a molar ratio of 0.2:1 or less, more preferred is to use a ratio of 0.16:1 or less and most preferred is to use a ratio of 0.1:1 or less. The molar ratio is based on the number of groups available for cross-linking on the cross-linker and on the chitosan. For the cross-linker it will depend on the functionality (bi-, tri-, tetrafunctional etc) and on the chitosan to the accessibility of the amino groups (only the deacetylated amino groups will be reactive). Clearly, the number of available amino groups will be determined by the degree of deacetylation of the chitosan.

We prefer the chitosan to have a degree of deacetylation below 75%, more preferred is to have a degree of deacetylation below 70%, even more preferred is a degree of deacetylation below 65% and even more preferred is a degree of deacetylation of less than 60% and most preferred is to have a degree of deacetylation of less than 55%. Chitin is completely insoluble in water solutions and becomes to some extent soluble when the degree of deacetylation is 30% or more. We prefer to have a degree of deacetylation above 35%, preferred is a degree of deacetylation above 40% and most preferred is a degree of deacetylation above 45%. The solubility of chitosans is also dependent on parameters like molecular weight, distribution of acetyl groups within the chain and counter ions. Chitosan is polydisperse in its nature, i.e. contains a mixture of different chain lengths. Commercially chitosans are characterised by their viscosity and an average molecular weight is given. We prefer to have a viscosity of up to 15,000 mPas, preferably from 2 to 10,000 mPas, more preferably from 5 to 2,000 mPas and most preferably from 10 to 1,000 mPas when measured as a 1% w/v solution in 1% aqueous acetic acid at a temperature of 25° C. using a rotating viscometer with a spindle rotating at 20 rpm. The viscosity of the solution is an indication of the average molecular weight of the chitosan, it being understood that chitosan is a polymeric material having a distribution of molecules of varying chain length. We prefer to use chitosan solutions having a concentration of 3% or less. More preferred is to use a concentration of 2% or less. We prefer to have a concentration above 0.3% (w/w).

The pattern of the deacetylation of the chitosan is also important for its properties. The chitosan of the present invention must be randomly deacetylated. That is, large blocks of chitin-like polymer are to be avoided as such materials have a tendency to be less soluble. Instead, the chitosan of the present invention has a random pattern of acetylated and deacetylated monosaccharide units. One way of determining the nature of the monosaccharides is to determine the nearest-neighbour frequencies using NMR and compare the frequencies obtained with statistical models, see WO 03/011912.

Commercially available chitosan typically has the non-random, block structure. The reason for this is that chitin is isolated in solid phase processes from crustacean shells. In such processes, in which the shells remain undissolved throughout the process, the shells are treated with strong alkali to give the partially deacetylated chitosan. However, because the chitin is initially in the form of crustacean shell, the hydroxide ions of the alkali tend to act preferentially on the monosaccharide units on the surface of the shell; the monosaccharide units within the centre of the relatively thick shell tend not to see the hydroxide ions and hence retain the N-acetyl substitution pattern.

In order to avoid these chitin-like blocks, the chitin/chitosan polysaccharide chains should be treated in solution. This enables the polysaccharide chains to enter solution and the structure of the shell is lost. This enables a random deacetylation pattern. This may be achieved by treating the chitin in solution under carefully controlled conditions, or by fully deacetylating the chitin and then reacetylating in solution to provide the required degree of deacetylation. See T. Sannan et al. Makromol. Chem. 177, 3589-3600, 1976, X. F. Guo et al. Journal of Carbohydrate Chemistry 2002, 21, 149-61 and K. M. Vårum et al. Carbohydrate Polymers 25, 1994, 65-70. The chitosan of the present invention is preferably obtainable by acetylating and/or deacetylating the chitosan in the solution phase to provide a random deacetylation pattern.

When cross-linking of low deacetylated chitosan is performed we prefer to have reaction conditions where pH is above 6 and where the chitosan does not precipitate. Even more preferred is to use pH above 6.5 and most preferred is to use a pH above 7.0. It is also preferred to use a pH that does not to a substantial degree destroy the cross linking reagent by hydrolysis or via an elimination reaction. Typical conditions for said reaction are alkaline conditions and we prefer to use a pH below 10, more preferred is to use a pH below 9.5 and even more preferred is to use pH below 9.0. Preferably, the water is present at 97-99.7%. An additional solvent may also be used, such as ethanol, e.g. at 0.2% (v/v). The concentration of the cross-linking agent used in the cross-linking reaction is preferably 0.01-0.2% (v/v), more specifically about 0.02% (v/v).

The viscoelastic hydrogel according to the invention is obtained as a block which may be isolated without further treatment. The hydrogel is then processed to provide smaller blocks or fragments using conventional techniques known in the art. This resulting "crushed gel" is injectable through a fine needle. The viscosity of the gel can be measured with a rheometer, as set out in Example 16.

The present invention will now be illustrated by, but not limited to, the following examples.

EXAMPLES

The following materials were used in the Examples unless otherwise stated:

Chitosans of low degree of N-deacetylation were prepared essentially following the principles outlined in: Sannan T, Kurita K, Iwakura Y. Studies on Chitin, 1. Die Makromolekulare Chemie 1975; 0:1191-5, Sannan T, Kurita K, Iwakura Y. Studies on Chitin, 2. Makromol. Chem. 177, 3589-3600, 1976, Guo X, Kikuch, Matahira Y, Sakai K, Ogawa K. Water soluble chitin of low degree of deacetylation. Journal of Carbohydrate Chemistry 2002; 21:149-61 and O 03/011912.

Example 1

Chitosan (1.11 g, degree of N-deacetylation 50%, MW 145 kD) was suspended in 70 mL distilled water and 2M HCl (aq) was added dropwise in order to dissolve the chitosan. The pH of the solution was adjusted to 7.4 with 1M sodium hydroxide. The volume was adjusted to 100 mL with distilled water. 3,4-Diethoxy-3-cyclobutene-1,2-dione (122 µL of a 20% (v/v) solution in ethanol) was added and the solution was stirred for 3 h. The pH of the solution was adjusted to 8.3 and the volume was adjusted to 111 mL. The solution was placed in a heating cabinet at 40° C. for 3 days. The solidified gel was designated as 1-1. The procedure was repeated but no 3,4-diethoxy-3-cyclobutene-1,2-dione was added. This gel was designated as 1-2.

Example 2

Chitosan (0.50 g, degree of N-deacetylation 72%, MW 145 kD) was suspended in 35 mL distilled water and 2M HCl (aq) was added dropwise in order to dissolve the chitosan. The pH of the solution was adjusted to 6.2 with 1M sodium hydroxide. The volume was adjusted to 50 mL with distilled water. This gel was designated as 2-1. To 20 mL of the above solution was added 3,4-diethoxy-3-cyclobutene-1,2-dione (40 µL of a 12% (v/v) solution in ethanol) was added and the solution was vigorously stirred for 10 minutes. The pH of the solution was adjusted to 7.5. The solution was placed in a heating cabinet at 40° C. for 3 days. The solidified gel was designated as 2-2.

Example 3

Chitosan (0.50 g, degree of N-deacetylation 72%, MW 145 kD) was cross-linked with glutaraldehyde (6 g) in 50 mL 1M HOAc (aq) at 100° C. The reaction conditions were as described in J. Control. Release 111 (2006), 281-289.

Example 4

1 g of each of the gels according to Examples 1-4 was subjected to 1M NaOH (aq). The chitosan of gels 1-2, 2-1, and 3 (comparative) precipitated, whereas the cross-linked gels 1-1 and 2-2 (invention) remained clear.

Example 5

Chitosan hydrochloride (0.50 g, degree of N-deacetylation 55%, MW 145 lcD) was dissolved in 45 mL water. The pH of the solution was adjusted to 7.3 with diluted sodium hydroxide. 3,4-Diethoxy-3-cyclobutene-1,2-dione (102 µL of a 12%

(v/v) solution in ethanol) was added and the solution was stirred for 3 h. The pH of the solution was adjusted to 8.3 and the volume was adjusted to 50 mL. The major cat allergen, Fel d 1 (5.9 mg), was added to 3 g of the above solution and the mixture was transferred to a 5 mL vial and left for 6 days at 40° C. The resulting gel was mechanically processed and transferred to a 1 mL syringe.

Example 6

Hyaluronic acid (50 mg) was dissolved in MES buffer (20 mL, 20 mM, pH 6.5). The viscoelastic hydrogel according to Example 5 (4 mL) was added to the hyaluronic acid solution and placed on an orbital shaker board for 90 minutes. The coated gel was centrifuged at 2,300 rpm for 2×10 minutes, washed with PBS buffer and transferred to a syringe. This hyaluronic acid coated chitosan gel could be lyophilised and rehydrated to yield a viscoelastic gel. When the hydrogel according to Example 5 was added to PBS buffer with no hyaluronic acid the thread-like fragments became whitish and sticky and could not easily be isolated and thus could not be rehydrated.

Example 7

Chitosan hydrochloride (0.30 g, degree of N-deacetylation 55%, MW 145 kD) was dissolved in 25 mL water. The pH of the solution was adjusted to 8.3 with diluted sodium hydroxide and the volume adjusted to 3.0 g. 3,4-Diethoxy-3-cyclobutene-1,2-dione (61 µL of a 12% (v/v) solution in ethanol) was added and the solution was stirred for 3 h and than the mixture was left for 6 days at 40° C. 6 mg Fel d 1 was added to this solution and the mixture was stirred. The mixture was then transferred to a 1 mL syringe.

Example 8

Comparative

Chitosan hydrochloride (0.90 g, degree of N-deacetylation 81%, MW 145 kD) was suspended in 27 g distilled water. The pH of the solution was 16. PBS (2.0 ml, 25 mM, pH 7.4) was added. The pH was adjusted to 5.8 with diluted sodium hydroxide and the volume was adjusted to 60 mL. 2.27 mg Fel d 1 was mixed with 1.1 mL of the above solution and was transferred to a 1 mL syringe.

Example 9

Groups of BALB/c mice were injected subcutaneously, in the neck region, with 100 µL of the solutions according to Examples 5, 7 and 8. The mice were then sacrificed at different time-points, after 1, 7 and 21 days. The mice were sacrificed by inhalation of $CO_2$. The skin at the injection site was collected and placed in histocon on ice and the skin samples were then frozen in an acetone bath. The frozen skin biopsies were kept at −80° C. before histological section. The histological sections were then analyzed for cell infiltration. The histological examination showed a massive infiltration of cells already one day after the injection for the gels according to Examples 5 and 7. Histological examination of the gel according to Example 8 showed a lens shaped gel covered with cells on its surface but with no cells inside the gel. In gels 5 and 7 the cells had infiltrated the entire material after 24 h. After 7 days, the amount of chitosan was reduced for the gels of Examples 5 and 7. Two weeks later, day 21, there was almost no sign of the injected material, whereas the gel of Example 8 showed a much slower colonisation of cells and also a much slower degradation.

FIG. 1 shows histological sections from the injection sites of mice 24 hours after subcutaneous injection with the viscoelastic chitosan gel of Example 5 (FIG. 1(a)) and the reference chitosan of Example 8 (FIG. 1(b)), respectively. The results show that the gel of the present invention is infiltrated by immune cells faster and to a greater extent than the reference gel. Even after three weeks the reference chitosan still was not completely infiltrated, and a slower rate of degradation was observed for the reference chitosan gel compared to the gel of the invention.

Example 10

Groups of three BALB/c mice were injected subcutaneously, in the neck region, with 100 µL of the gel according to Examples 5, 7 and 8. A booster injection was given on day 64, 9 weeks after the first injection. Blood samples were then drawn form the tail artery 1, 2, 3, 9 and 10 weeks after injection. The levels of Fel d 1-specific serum $IgG_1$ and IgE were measured by ELISA. All the gels gave rise to a $IgG_1$-antibody response.

Example 11

Chitosan (2.05 g, degree of N-deacetylation 50%, MW 145 kD) was suspended in 160 mL of distilled water and 2M HCl (aq) was added until the chitosan was dissolved. The pH was adjusted to 7.9 by dropwise addition of 1M NaOH (aq). The volume was adjusted to 200 mL with distilled water. 1,4-Butandiol diglycidylether (166 µL of a 5% (v/v) solution in ethanol) was added dropwise to 50 mL of the above solution. The mixture was stirred vigorously for 10 minutes at room temperature and then placed in a heating cabinet (50° C.) overnight.

Example 12

Chitosan (2.25 g, degree of N-deacetylation 55%, MW 145 kD) was suspended in 130 mL of distilled water and 2M aqueous hydrochloric acid was added until the chitosan was dissolved. The pH was adjusted to 6.75 with 1M sodium hydroxide and the volume was adjusted to 160 mL. To 50 mL of the above solution 3,4-diethoxy-3-cyclobutene-1,2-dione (120 µl, 12% solution in ethanol) was added and the solution was stirred for 2 h at room temperature. Diclofenac (773 mg) was dissolved in 25 mL of distilled water and added to the above solution. The pH of the solution was adjusted to 8.1 with 1M sodium hydroxide and the solution was sonicated for 1 h and then heated to 40° C. overnight. The resulting gel (1 g) was mixed with hyaluronic acid (4 g, 0.25% in distilled water). The gel was placed on in a Franz cell equipped with a Spectra/Por filter with having a molecular weight cut-off of 2000 Da and filled with PBS buffer. 38% of the diclofenac was released after 2 h, 60% after 5 h and 72% after 24 h.

Example 13

The procedure according to Example 5 was repeated with radioactively $^{75}$Se-labeled rFel d 1. Production of $^{75}$Se-labeled rFel d 1 was performed using in situ labelling of the selenocysteine residue in Sel-tagged rFel d 1, essentially as described previously for Der p 2 (Febs J 2005; 272:3449-60) but with the constructs, production and purification conditions for Sel-tagged rFel d 1 (Chembiochem 2006; 7:1976-81).

Example 14

In vivo tracking of 100 μg radioactively labelled [$^{75}$Se]rFel d 1 (2 μCi) coupled to chitosan or adsorbed to aluminium hydroxide was performed as previously described (Febs J 2005; 272:3449-60, Methods Enzymol 1981; 77:64-80). Briefly, mice (n=2/group) were s.c. injected with Chitosan-[$^{75}$Se]rFel d 1 or alum-[$^{73}$Se]rFel d 1 and killed after 24 hours or 1 week. The mice were frozen and processed for tape section autoradiography. The sections (60 μm) were pressed against X-ray film (Structurix, Agfa, Mortsel, Belgium) and developed using D19 (Kodak, Rochester, USA).

Results: After 24 h the radioactivity had been metabolised and was detected in e.g. the liver and spleen. The pattern was similar to that of aluminium hydroxide. After 1 and 2 weeks respectively only trace amounts of radioactivity could be detected.

Example 15

Chitosan (3.6 g, degree of N-deacetylation 52%,) was suspended in 250 mL of distilled water and 2M HCl (aq) was added until the chitosan was dissolved. The pH was adjusted to 7.0 by dropwise addition of 1M NaOH (aq). The volume was adjusted to 300 mL with distilled water. This solution was designated solution X (1.2% chitosan). To 100 mL of solution X 50 mL of water was added, this solution was designated solution Y (0.8% chitosan). 16 mL of solution X and solution Y, respectively, was added to two beakers for each solution. To each, different amounts of 3,4-diethoxy-3-cyclobutene-1, 2-dione (10% (v/v) solution in ethanol) was added according to list below.

| | |
|---|---|
| X-1 | 20 μL |
| X-2 | 59 μL |
| X-3 | 118 μL |
| Y-1 | 29 μL |
| Y-2 | 88 μL |
| Y-3 | 176 μL |

The mixtures were stirred vigorously, for 10 minutes at room temperature and then 4 g of each solution was transferred to Petri dishes (d=35 mm), sealed and placed in a heating cabinet (40° C.) for 4 days.

Cylinders of diameter 6 mm and height 2.65±0.55 mm were extracted from the Petri dishes and the gel discs were compressed using an Instron 3345 equipped with a 100 N load cell. The samples were subjected to 1 min/min compression.

It should be mentioned that gels based on the 0.8% chitosan solution (Y-1, Y-2, Y-3) were technically more difficult to handle due to their less rigid structure and hence analytical precision was reduced compared to the gels based on the 1.2% chitosan solution (X-1, X-2, X-3). Although this needs to be taken into account when comparing analytical data, the gel is not adversely affected (indeed, a less rigid structure can make the gel easier to crush). Analytical data based on the measurements of the 1.2% gels (X-1, X-2, X-3) showed that the average E-modulus increased from 4.7 to 14.1 MPa when the amount of cross-linking agent increased from 2 to 12% (calculated as a ratio between the cross-linking agent and monosaccharide units).

Example 16

Chitosan (4 g, degree of N-deacetylation 55%) was suspended in 350 mL of distilled water and 2M HCl (aq) was added until the chitosan was dissolved. The pH was adjusted to 7.0 by dropwise addition of 1M NaOH (aq). The volume was adjusted to 400 mL with distilled water. Two different volumes of 3,4-diethoxy-3-cyclobutene-1,2-dione (60 (sample 1) and 185 μL (sample 2) of a 12% (v/v) solution in ethanol) were added dropwise to two different beakers containing 50 mL of chitosan solution. The mixtures were stirred vigorously for 5 minutes at room temperature and then 8 mL were transferred to plastic syringes (10 mL). The syringes were sealed and placed in a heating cabinet (40° C.) for 72 h. The formed gels were then transferred to a new syringe (5 mL syringes) by pressing them through a silicon tube (d=3 mm). The syringes were stored at 4° C. before measurement.

For rheology studies a Bohlin Gemini VOR instrument was used, using for measurement cell the cone-plate geometry of 40 mm diameter and a cone angle of 4 degrees. All measurements were performed at 25° C.

Storage and loss moduli G' and G" were studied in oscillatory shear experiments. The rheological parameters reflect solid and liquid viscoelastic properties, respectively.

Both gel samples showed the properties of a viscoelastic soft solid in the strain sweep measurement with G'>G", i.e. the elastic component is larger than the liquid counterpart. Within the stable linear region G' (1 Hz) was around 450 Pa with a phase angle of ca 1° for sample 1. For sample 2 the corresponding data was G' ca. 900 Pa and a phase angle of 1°.

The second type of oscillatory measurements made on the same preparations was frequency sweeps for a constant deformation of 0.5. The following observations were made: sample 2 gel is of higher gel strength, increased elastic modulus G' than sample 1 gel, and both samples show an apparent frequency independent elastic modulus in the studied range of 0.1 to 20 Hz.

It is possible to make reproducible viscoelastic measurement on fractured versions of the gel samples. The two gel samples show essentially the same viscoelastic properties in their fractured state. Gel sample 2 is of increased gel strength compared to sample 1.

Example 17

Chitosan (1 g, degree of N-deacetylation 55%) was suspended in 80 mL of distilled water and 2M HCl (aq) was added until the chitosan was dissolved. The pH was adjusted to 6.8 by dropwise addition of 1M NaOH (aq). The volume was adjusted to 100 mL with distilled water. PEG1600 (2.5 g, 40% dissolved in water) and 3,4-diethoxy-3-cyclobutene-1, 2-dione (183 μL of a 1% (v/v) solution in ethanol) were added dropwise under stirring to 7.5 g of the chitosan solution. The solution was placed in a heating cabinet at 40° C. for 3 days to give a transparent viscoelastic gel.

Example 18

Chitosan (1.5 g, degree of N-deacetylation 55%) was suspended in 80 mL of distilled water and 2M HCl (aq) was added until the chitosan was dissolved. The pH was adjusted to 6.5 by dropwise addition of 1M NaOH (aq). The volume was adjusted to 100 mL with distilled water. Metagin (0.2 g) and propagin (0.03 g) dissolved in 23 g water was added to 67 g of the chitosan solution and stirred for 18 h at room temperature, 3,4-Diethoxy-3-cyclobutene-1,2-dione (24.6 uL of a 11% (v/v) solution in ethanol) was added dropwise to the above solution. The solution was placed in a heating cabinet as described in Example 17.

The invention claimed is:

1. A viscoelastic hydrogel comprising a randomly deacetylated chitosan having a degree of deacetylation between 30 and 75%, wherein the chitosan is crosslinked with diethyl squarate at a molar ratio of the diethyl squarate to the chitosan of 0.2:1 or less based on the number of functional groups in the diethyl squarate and the number of deacetylated amino groups in the chitosan, and wherein the viscoelastic hydrogel is stable to processing into smaller, individually separated gel fragments.

2. A viscoelastic hydrogel as claimed in claim 1, wherein the chitosan has a degree of deacetylation of between 35 and 55%.

3. A viscoelastic hydrogel as claimed in claim 1 or 2, wherein the chitosan, prior to cross-linking, has a weight average molecular weight of 10-500 kDa.

4. A process for preparing a viscoelastic hydrogel of claim 1 comprising providing a randomly deacetylated chitosan in an aqueous solution, cross-linking the randomly deacetylated chitosan with diethyl squarate and isolating the resultant viscoelastic hydrogel.

5. A process as claimed in claim 4, wherein the cross-linking is performed at a pH between 6 and 10.

6. A viscoelastic hydrogel obtained by the process of claim 4 or 5.

7. A viscoelastic hydrogel as claimed in claim 6 in the form of a crushed gel.

8. A viscoelastic hydrogel as claimed in claim 6 for use as a vaccine, in drug delivery, in tissue augmentation, as a cell culture scaffold, for encapsulation of viable cells, in wound healing devices, in orthopaedics, as a biomaterial, for treating urinary incontinence or vesicoureteral reflux, in viscosurgery, in providing living cells to a host organism, as a cosmetic, as a bulking agent, as a thickener, as an additive in the food industry, as a glue, as a lubricants, or as a drilling servicing fluid.

9. A pharmaceutical composition comprising the viscoelastic hydrogel as claimed in claim 6 and a pharmaceutically active ingredient.

10. An immunological agent comprising the viscoelastic hydrogel as claimed in claim 6 and an antigen, wherein the antigen is optionally covalently bonded to the chitosan.

* * * * *